US007830515B2

(12) United States Patent
Murray et al.

(10) Patent No.: US 7,830,515 B2
(45) Date of Patent: Nov. 9, 2010

(54) METHOD AND APPARATUS FOR DETECTION OF BIOAEROSOLS

(75) Inventors: George M. Murray, Columbia, MD (US); Cheryl S. Schein, Rockville, MD (US); David R. Kohler, Ocean Pines, MD (US); Jennifer L. Sample, Bethesda, MD (US); Jennifer A. Nix, Ellicott City, MD (US); Protagoras N. Cutchis, Highland, MD (US); Adam K. Arabian, Louisville, KY (US); Harvey W. Ko, Ellicott City, MD (US); Micah A. Carlson, Baltimore, MD (US); Michael P. McLoughlin, Sykesville, MD (US)

(73) Assignee: The Johns Hopkins University, Baltimore, MD (US)

( * ) Notice: Subject to any disclaimer, the term of this patent is extended or adjusted under 35 U.S.C. 154(b) by 64 days.

(21) Appl. No.: 12/141,298

(22) Filed: Jun. 18, 2008

(65) Prior Publication Data

US 2008/0254502 A1 Oct. 16, 2008

Related U.S. Application Data

(62) Division of application No. 10/503,168, filed as application No. PCT/US03/11723 on Apr. 16, 2003, now Pat. No. 7,494,769.

(60) Provisional application No. 60/373,080, filed on Apr. 16, 2002.

(51) Int. Cl.
*G01N 21/25* (2006.01)

(52) U.S. Cl. .......................... 356/417; 356/51; 356/432

(58) Field of Classification Search ................. 356/417, 356/432, 436–442
See application file for complete search history.

(56) References Cited

U.S. PATENT DOCUMENTS

| | | | | |
|---|---|---|---|---|
| 5,701,012 | A | | 12/1997 | Ho |
| 5,870,182 | A | * | 2/1999 | Abend et al. .................. 356/73 |
| 5,895,922 | A | | 4/1999 | Ho |
| 5,985,214 | A | * | 11/1999 | Stylli et al. ................... 422/65 |
| 6,593,582 | B2 | | 7/2003 | Lee et al. |

OTHER PUBLICATIONS

Peter P. Hairston et al., Design of An Instrument For Real-Time Detection of Bioaerosols . . . , J. Aerosol Sci, vol. 28, No. 3, pp. 471-487, 1997.

Li et al., Study of Properties on Non-Protected Room . . . , Specrochimica Acta Part A, vol. 57, pp. 385-393, 2001.

* cited by examiner

*Primary Examiner*—Tarifur Chowdhury
*Assistant Examiner*—Tara S Pajoohi
(74) *Attorney, Agent, or Firm*—Francis A. Cooch

(57) ABSTRACT

A method and apparatus for evaluating a bioaerosol sample is provided which includes detecting frequency and/or time resolution factors that allow discriminate between a plurality of signals emitted by the bioaerosol to selectively detect biological materials contained in the bioaerosol sample from materials of non-biological origin and potentially associated with a pathogenic bioaerosol.

13 Claims, 6 Drawing Sheets

```
    ┌──────────────┐
    │   COLLECT    │
    │  BIOAEROSOL  │──12
    │    SAMPLE    │
    └──────┬───────┘
           ▼
    ┌──────────────┐
    │   ADD EHAP   │
    │  AND OXYGEN  │──14
    │   SCAVENGER  │
    └──────┬───────┘
           ▼
    ┌──────────────┐         ┌──────────────┐
    │    EXCITE    │──16     │    DETECT    │
    │  COLLECTED   │────────▶│ FLUORESCENCE │──18
    │    SAMPLE    │         │              │
    └──────┬───────┘         └──────────────┘
           ▼
    ┌──────────────┐
    │  EXTINGUISH  │
    │  EXCITATION  │──20
    │    SOURCE    │
    └──────┬───────┘
           ▼
    ┌──────────────┐
    │    DETECT    │
    │ PHOSPHORESCENCE │──22
    └──────────────┘
```

FIG. 1

```
┌─────────────────────┐         70    ┌─────────────────────┐
│  ACTUATE VACUUM PUMP│────72    ↙    │ DELIVER BUFFERED    │
│  TO COLLECT AEROSOL │               │ WATER INTO SAMPLE   │
│  ON SOLID SURFACE   │         90 ─  │ VESSEL              │
└──────────┬──────────┘               └──────────┬──────────┘
           ↓                                     ↓
┌─────────────────────┐               ┌─────────────────────┐
│   ADD EHAP AND      │──94           │  ACTUATE VACUUM PUMP│
│  OXYGEN SCAVENGER   │          92 ─ │  TO COLLECT AEROSOL │
│                     │               │  IN SAMPLE VESSEL   │
└──────────┬──────────┘               └──────────┬──────────┘
           ↓                                     ↓
       ┌───────────────────────┐     ┌─────────────────────┐
  74 ─ │  TRANSPORT COLLECTED  │     │  ACTUATE PERISTALTIC│
       │  SAMPLE TO OPTICAL    │←────│  PUMP TO ADD EHAP TO│
       │  SYSTEM               │     │  COLLECTED SAMPLE   │
       └──────────┬────────────┘     └─────────────────────┘
                  ↓                           94
       ┌───────────────────────┐
  76 ─ │  POWER LIGHT SOURCE TO│
       │  EXCITE COLLECTED SAMPLE│
       └──────────┬────────────┘
                  ↓                       80
                 78                ┌──────────────┐
              ╱──────╲      NO     │   SAMPLE     │
             ╱ DETECT ╲────────────│   WASTE      │
             ╲FLUORESC╱             │  RESERVOIR   │
              ╲SIGNAL╱              └──────────────┘
                 │YES
                 ↓                    82
       ┌───────────────────────┐
       │  EXTINGUISH LIGHT     │
  98   │  SOURCE               │     86
┌──────┐└──────────┬────────────┘   ┌──────────┐
│SOUND │           ↓                │  SAVE    │
│SIGNAL│←─────    84     ──YES/NO──→│  SAMPLE  │
└──────┘        ╱──────╲             │ RESERVOIR│
  100          ╱ DETECT ╲             └─────┬────┘
┌──────┐      ╲PHOSPHOR╱                   │    88
│VISUAL│←─────╲SIGNAL ╱                    ↓
│SIGNAL│       ╲──┬───╱             ┌──────────────┐
└──────┘          └──────────────→  │  TRIGGER     │
                                    │ SOPHISTICATED│
                                    │  DETECTION   │
                                    │  SYSTEM      │
                                    └──────────────┘
```

FIG. 5

METHOD AND APPARATUS FOR DETECTION OF BIOAEROSOLS

CROSS-REFERENCE TO RELATED APPLICATIONS

This application is a divisional application of U.S. patent application Ser. No. 10/503,168, filed Jul. 30, 2004, issued Feb. 24, 2009, as U.S. Pat. No. 7,494,769, which is a 371 of PCT/US03/11723 filed Apr. 16, 2003, which claims the benefit of U.S. Provisional Application Ser. No. 60/373,080, filed on Apr. 16, 2002, the contents of which are incorporated herein by reference.

BACKGROUND OF THE INVENTION

1. Field of the Invention

The present invention generally relates to a sampling methodology. PMore particularly, the present invention is directed to a method and apparatus utilizing a luminescence spectroscopy to detect bioaerosols and alert of the presence of a potentially pathogenic bioaerosol.

2. Description of the Related Art

Aerosols of biological origin, whether formed intentionally or unintentionally, represent a potential threat of infection by pathogens. This threat is particularly daunting in the context of closed spaces, such as buildings. A variety of methods directed to identifying harmful biological materials are known. One of the known methods is based on the principles of the luminescence spectroscopy and is concerned with the production, measurement, and interpretation of electromagnetic spectra arising from either emission or absorption of radiant energy by various substances.

One aspect of the luminescence spectroscopy provides for the ability of biological materials to fluoresce due to the presence of proteins that possess certain amino acids. Fluorescence occurs when fluorophores and fluorescent particles absorb light at a given wavelength and then immediately emit light at a longer wavelength. Although not all particles fluoresce, some bio-aerosols contain intrinsic fluorophores that could potentially be used to tag the sample as a bioaerosol. Common fluorophores found in bioaerosol are, for example, Nicotinamide Adenine Dinucleotide (NADH), Tryptophan, Tyrosine, and Riboflavin. Each of these flurophores is characterized by respective peak excitation and corresponding emission wavelengths.

The primary fluorescent amino acids are tyrosine and tryptophan. The latter compound absorbs and emits at longer wavelengths and is less likely to have spectral overlaps with compounds that are not of a biological origin. However, there are still many environmental elements and hydrocarbons that will also fluoresce in the same wavelength as tryptophan, let alone the rest of the above-mentioned fluorophores.

Another aspect of the luminescence spectroscopy that may provide a tool for detecting biological materials is phosphorescence. As compared to fluorescence, phosphorescence is characterized by the time delay emission signal that allows for time-resolution to be used as a discriminator between samples that fluoresce versus those that phosphoresce. Hence, it is possible to delay the detection of the signal until after the light source has been extinguished and the fluorescent signal has disappeared. In addition to the time delay, Tryptophan phosphoresces at a longer emission wavelength.

Most of the known biological detectors incorporate fluorescence as a means for detecting the presence of a biological aerosol. Although fluorescence is a relatively simple approach, its major disadvantage, as discussed above, is the low selectivity for the bioaerosols of interest.

Current biological aerosol detection/triggering technology including the Biological Aerosol Warning Sensor (BAWS) developed by the Massachusetts Institute of Technology and the ultra Violet Aerodynamic Particle Sizer (UVAPS) developed by TSI is acceptable. However, these instruments are expensive, power hungry, large, and require complex algorithms to determine relatively little information.

A need, therefore, exists for a methodology either perfecting or complementing a fluorescence detection technique and for an inexpensive, low power, robust apparatus carrying out the inventive methodology.

Thus, one of the objects of the present invention is to provide a method for detecting pathogenic bioaerosols having a secondary detection technique to complement fluorescence.

Another object of the present invention is to provide an apparatus for carrying out the inventive method and capable of effectively collecting bioaerosols and selectively detecting the presence of the biological materials of interest contained in the bioaerosols.

Still another object of the present invention is to provide the inventive apparatus adapted to generate a warning upon detecting the biological materials of interest and to trigger secondary, more sophisticated, equipment for the confirmation of the initially detected materials and their further identification.

A further object of the present invention is to provide the inventive apparatus characterized by a simple, space- and cost-efficient structure.

Yet another object of the invention is to provide a detection system including multiple inventive apparatuses and deployed in a single location to provide added discrimination of actual threat levels.

SUMMARY OF THE INVENTION

These and other objects have been achieved by a new method, characterized by the collection of bioaerosols and further excitation of a sample thereof to controllably discriminate between biomaterials that fluoresce versus those that phosphoresce. The latter would indicate the probability of the presence of biological materials of interest in the excited sample.

The inventive method utilizes both fluorescence vs. fluorescence-based detection as well as fluorescence vs. phosphorescence-based detection. The optical system of the inventive sensor includes two optical channels both operative to detect fluorescence signals emitted at different wavelengths and associated with different bioagents. However, in addition to exclusively detecting fluorescence, one of the optical channels is also configured to detect phosphorescence after the detection of the fluorescence has been completed.

In the case of fluorescence vs. phosphorescence, if the former is detected by one of the optical channels, the possibility of the presence of a biomaterial of interest exists. Subsequent detection of the phosphorescence during the second stage indicates the probability of the presence of the biomaterial of interest. Since the inherent advantage of phosphorescence over fluorescence is the time delayed emission signal, the inventive apparatus is operative to allow for time-resolution to be used as a discriminator between samples that fluoresce versus those that phosphoresce. As a result, the two-stage inventive method maximizes the probability of detection and minimizes the number of false alarms.

In accordance with another aspect of the inventive method, a heavy atom perturber that has chemical affinity for association with the molecules, whose phosphorescence is desired, is bonded with the sampled material. As a consequence, if a biological agent to be detected is present in the sampled material, phosphorescence occurs at a known wavelength.

A further aspect of the present invention provides for an apparatus operative to carry out the inventive method. The inventive apparatus includes mechanical, optical, and electronic sub-systems controllably cooperating with one another to collect a sample of bioaerosol, optically excite it and electronically process emitted signals to detect the presence of the biomaterials of interest.

One of the advantages of the inventive apparatus is based on the characteristic of the phosphorescence to emit light waves at wavelengths after a light source has been extinguished. By configuring a two-channel optical system and providing an electronic processing unit with software, which executes on the processing unit, the desired sequence of mechanical, optical and electronic operations leading to the minimization of false alarms and the maximization of detection is established and maintained. This, of course, does not eliminate the possibility of simultaneously detecting different fluorescence intensities by both optical channels, only one of which is configured to detect phosphorescence in addition to the ability to detect fluorescence.

In accordance with a further aspect of the present invention, phosphorescence of the biomaterials of interest at room temperature is induced by controllably adding a heavy atom perturber to the sample in the presence of an oxygen scavenger. The latter is used to minimize the possibility of the fluorescence of non-biological materials. As a result, the apparatus can indicate the presence of the biomaterial of interest based on its phosphorescence without, however eliminating the detection of this material based on its fluorescence.

While the inventive apparatus can be used for a variety of purposes, desirably it can be associated with a plurality of identical apparatuses or sensors to provide a network operative to alert building, office and/or industrial site occupants of the presence of a potentially pathogenic bioaerosol. Simplicity of the inventive structure and its space-efficient configuration can be used to construct a warning system capable of generating a real time detection/information about bioagents of interest and of triggering a more sophisticated system to confirm and identify these bioagents.

BRIEF DESCRIPTION OF THE DRAWINGS

The above and other objects, features and advantages will become more readily apparent from the following detailed description accompanied by the drawings, in which:

FIG. 1 is a flow chart illustrating an inventive method for detecting bio-aerosols;

FIG. 5 is a flow chart illustrating the operation of the processor of the electronic system diagrammatically illustrated in FIG. 4.

DETAILED DESCRIPTION OF THE PREFERRED EMBODIMENTS

Figure 2:
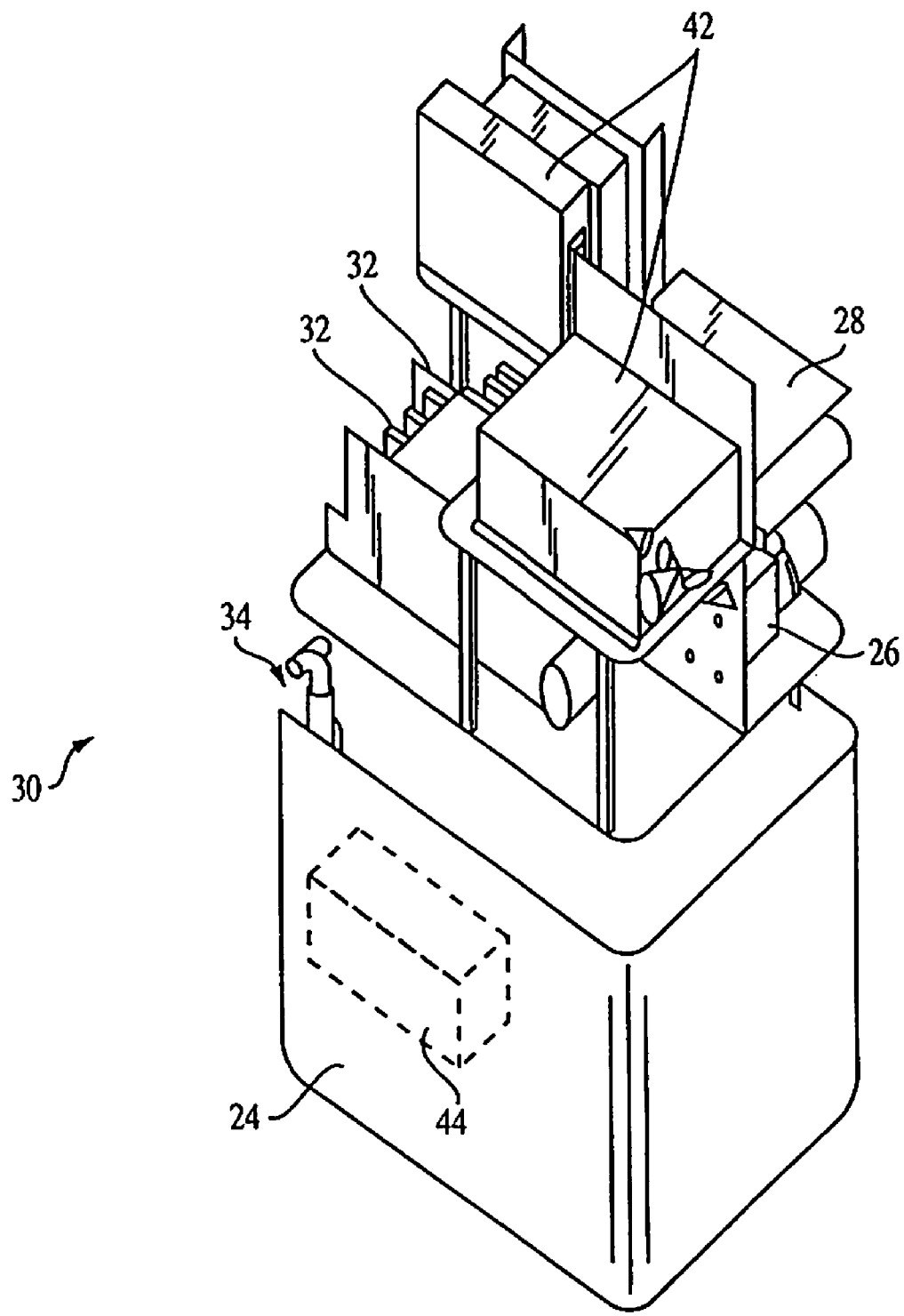
FIG. 2 is a perspective simplified view of an apparatus carrying out the inventive method of FIG. 2.

FIG. 1 illustrates an inventive method 10 based on the realization that hazardous biological materials dispersed in a particulate-containing airstream emit phosphoresce radiation at room temperature if bonded with an external heavy atom perturber (EHAP) in the presence of an oxygen scavenger, e.g., sodium sulfite.

In accordance with the above-stated inventive concept, the method 10 provides for the collection of a bioaerosol sample, as indicate by step 12. Following the collection of the bio-aerosol sample, the latter is mixed with an EHAP. Among EHAPs for use herein, include, for example, one or more of potassium iodide, lead, thallium, lutetium, gallium, cesium, and barium each of which advantageously have a sufficient chemical affinity for association with the molecule of fluorophores contained in an airstream. Common fluorophores found in aerosols that can potentially be used to tag the collected aerosol sample are, for example, NADH, Tryptophan, Tyrosine, Riboflavin and the like. For example, if Tryptophan is complexed with an EHAP, as indicated by step 14 of FIG. 1, it will phosphoresce when excited at a predetermined excitation wavelength, as shown by step 16. To provide distinct phosphorescence, it is desirable to reduce the fluorescent radiation generated by the materials of interest at a shorter wavelength by mixing the sample of bioaerosol with an EHAP in the presence of the oxygen scavenger. Ox However, the fluorescence radiation can be indicative of biological materials of interest and neglecting a fluorescent signal may lead to catastrophic results. As a consequence, the inventive method 10 provides for the detection of fluorescence, as an initial detection technique, as shown by step 18 of FIG. 1. Moreover, the inventive method can be utilized to provide for simultaneous detection of two or more fluorescence signals having different intensities, each of which may be associated with a respective bioagent contained in the collected bioaerosol.

Criticality of phosphorescence versus fluorescence in the context of the method 10 is the time delayed emission signal associated with the former and allowing for time-resolution to be used as a discriminator between the detected biomaterials that fluoresce against those that phosphoresce. The time delay is an advantage because it is possible to delay the detection of the signal until after the light source has been extinguished, as will be explained in detail below. Another critical characteristic associated with phosphorescence when compared with fluorescence is the different wavelengths of the emitted signals. For example, when excited with 285 nm light, Tryptophan will fluoresce at 360 nm, but it will phosphoresce at 450 nm. The above-identified differences are important to the inventive method providing for extinguishing an excitation source during step 20 to finally determine the probability of the presence of biological agents or biomaterials of interest if a phosphorescent signal is detected during step 22. Accordingly, the inventive method advantageously employs a two-stage fluorescence/phosphorescence detection technique allowing for a sequential identification of bio-materials of interest. Also, the inventive method allows for detection of two fluorescent signals associated with different wavelengths and intensities, which can be indicative of different fluorophores.

Turning now to FIGS. 2-5, a sensor 30 is able to detect bioaerosols based on a dual channel luminescence detection technique in accordance with the inventive method. The sensor 30 is a compact device having dimensions, which are approximately 12"×16"×8". In addition, as will become clear from the following description, the sensor 30 has a simple and cost efficient structure allowing, thus, the sensor to be placed in large quantities in a building to alert building occupants of potentially dangerous biomaterials contained in air.

As shown in FIG. 2, the sensor 30 comprises three primary units including at least a mechanical system, an optical system and an electronic system. The mechanical system is configured to collect a sample and transport the latter to the optical system operative to excite, emit and detect emission signals having wavelengths of interest. The electronic system is adapted to process the emissions signals and control the desired sequence of operations established to carry out the inventive method 10. These systems of the sensor 30 are packaged in a housing 24 made from a material capable of withstanding mechanical loads to preserve the functionality of the entire system even under adverse conditions.

The mechanical system includes at least a particle sampler or collector/concentrator as generally indicated as 34 (FIG. 2) and operative to rapidly provide the sample in a form that can be processed by the optical system. There are several issues that make sampling for biological agents particularly challenging. The first issue is that the sampling is normally targeted at living organisms; therefore, the technology must not "harm" the sample. Secondly, the target bio-material is generally only one component of a complex matrix of biological elements and chemical compounds that may affect the detection process, so the sample must often be purified to some extent. Lastly, the sample must be highly concentrated for a rapid analysis. An air-liquid surface virtual and/or real concentrator and/or an air-solid surface concentrator can readily deal with all of the above-discussed issues within the scope of the invention. As the names indicate, the former provides for the impingement of airborne particulates upon a reservoir filled with liquid, whereas the latter features a solid surface such as a bare or coated with mineral oil vacuum grease tape, paper, metal or any other suitable solid surface. Both types of the impactors are utilized within the scope of the present invention, as will become more readily apparent from the following description. In practical terms, a sampling stage is initiated upon actuation of a vacuum pump directing an airstream 36 (FIG. 3) through the concentrator into a sample vessel or collector 38 (FIG. 3), which is located downstream from the impactor. Depending on the particular test, a sample collector 38 can be configured to have a fluid reservoir or a solid surface both serving as a particle impinging and collecting concentrator.

Figure 3:
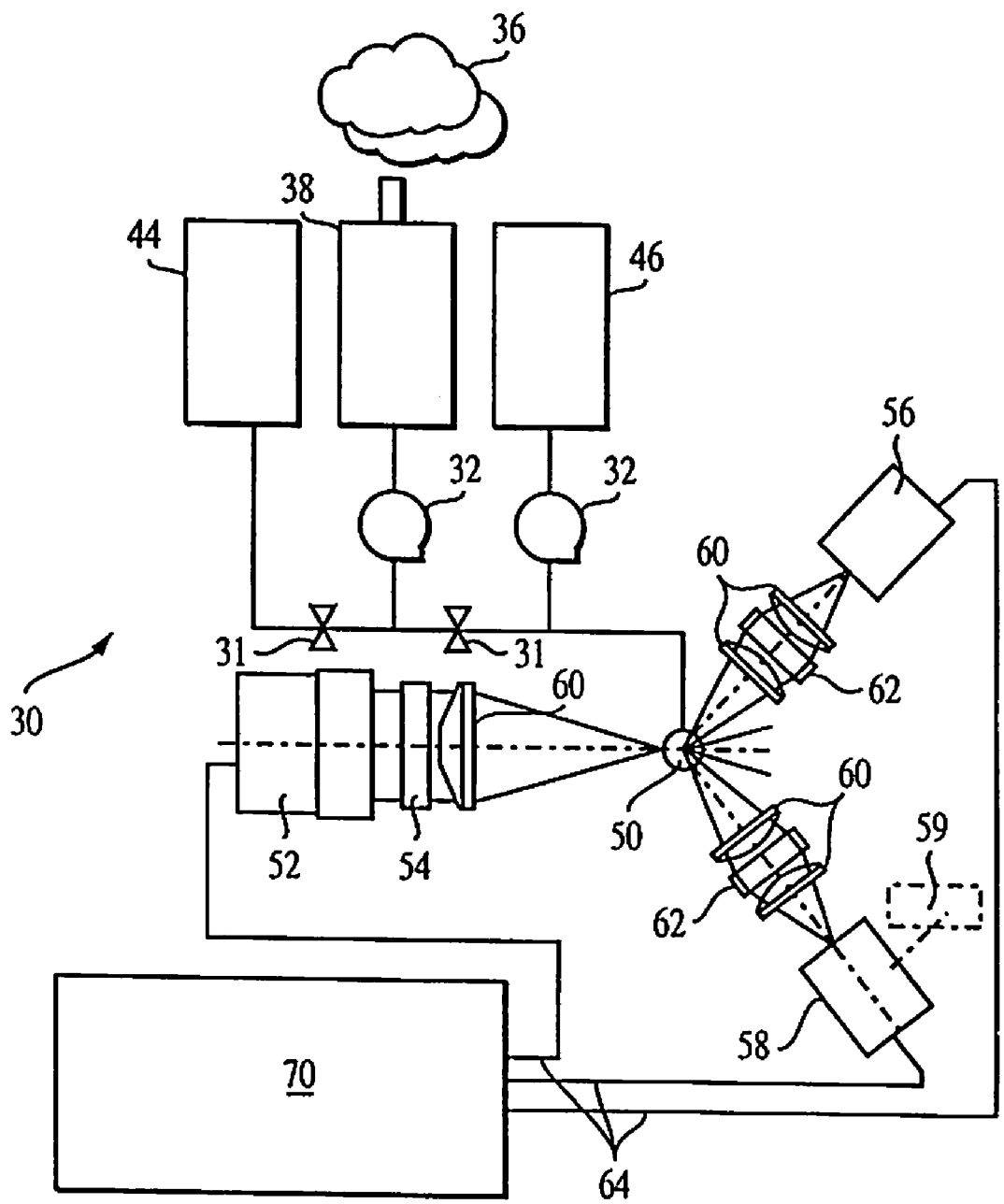
FIG. 3 is a schematic diagram of the fluidics and electro-optics systems of the inventive apparatus shown in FIG. 2.
Figure 4:
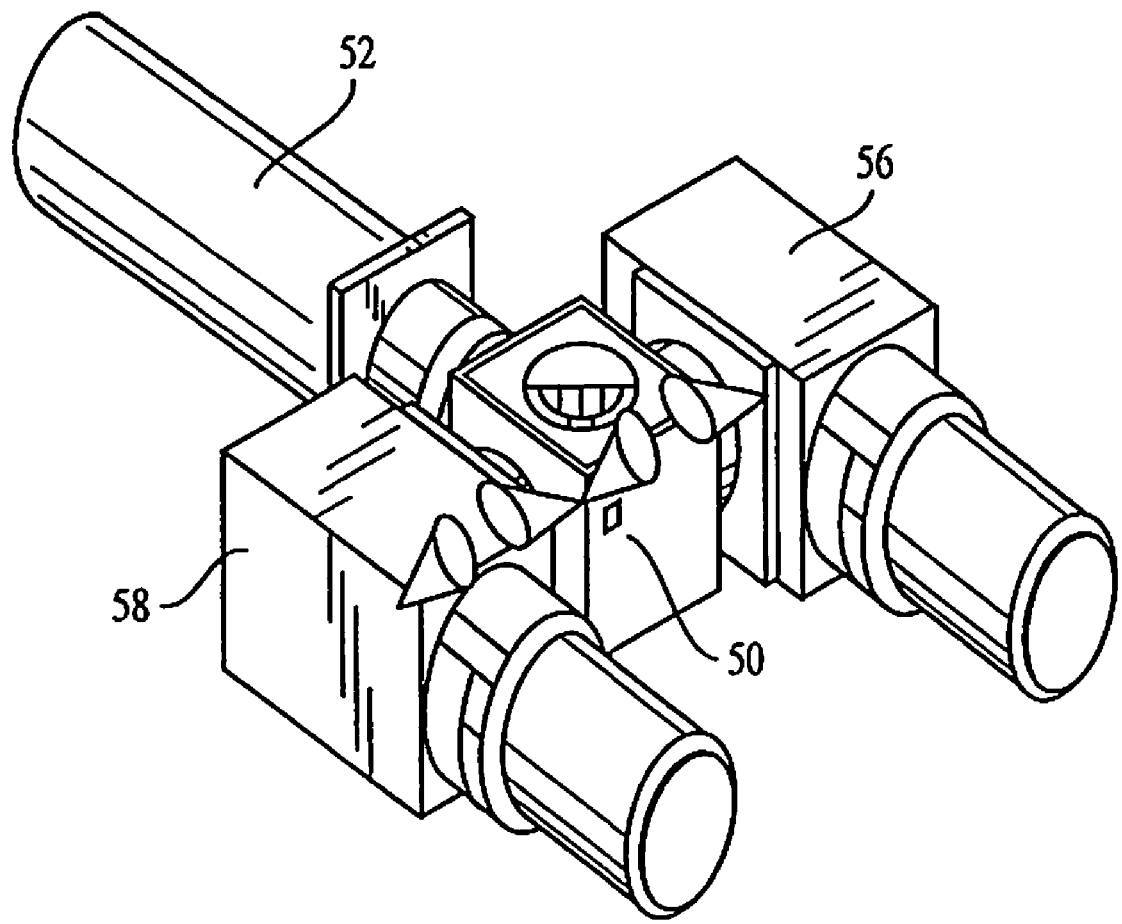
FIG. 4 is a simplified perspective view of the optic system shown in FIG. 3.
Figure 6:
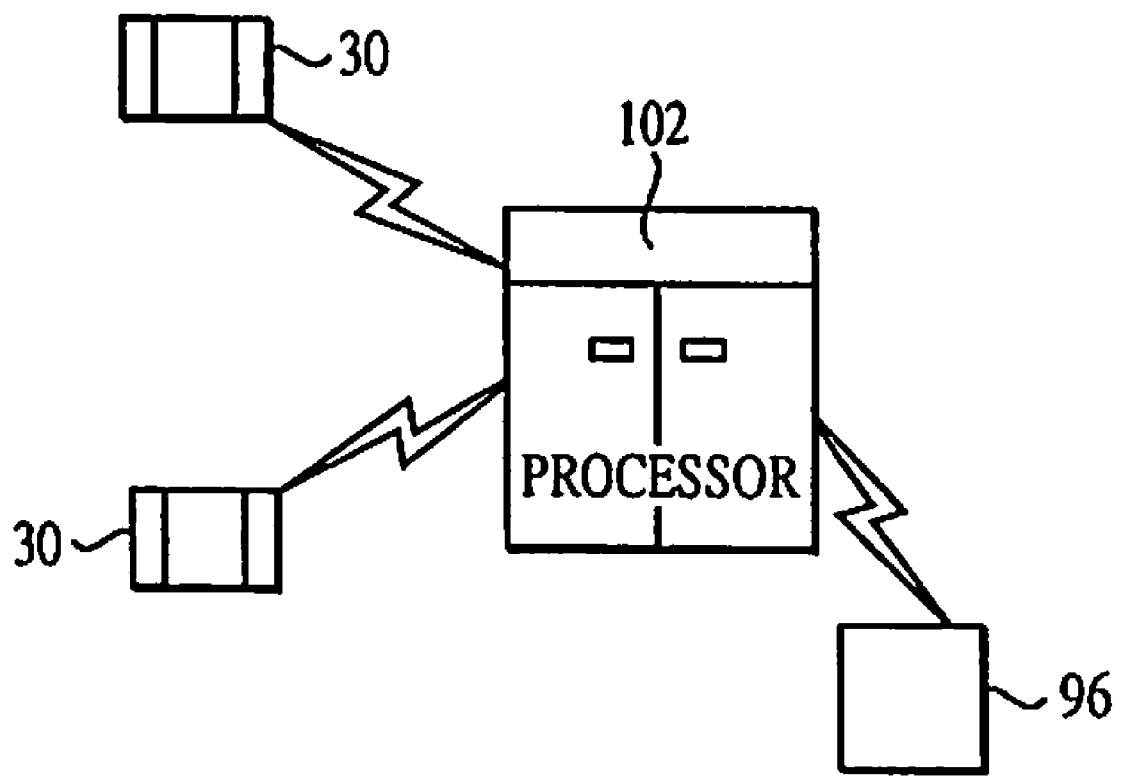
FIG. 6 is a schematic diagram of a warning system installable in a building.

If the collector 38 features a liquid surface, the mechanical system is provided with a sample of a fluid reservoir 44 (FIGS. 2 and 3), which is in fluid communication with the collector. Particularly, a fluidic control scheme includes a controllable first pinch valve 31 opening in response to a signal generated by the electronic system and simultaneously with actuation of a peristaltic pump 32. As a result, buffered water from the reservoir 44 is first pumped into the collector 38, which, in this case, is an impinger type of aerosol to liquid collector. After the aerosol has been collected, the liquid sample is delivered through another controllable pinch valve 31 to an optical cell 50, which can be associated with either a flow through cuvette or a closed cuvette (FIG. 3).

In accordance with one aspect of the inventive concept provided for detection of fluorescence and phosphorescence, as the sample is transported towards the cell 50, it is mixed with chemicals, i.e., the heavy atom perturber and oxygen scavenger. Particularly, the sample is bonded with the EHAP stored in a chemical reservoir 46 (FIG. 2) and controllably delivered into a sample path upon actuation of another peristaltic pump 32. Note that various types of pumps and valves are contemplated with the scope of invention and subject only to local objectives and experimentation.

Alternatively, if the collector 38 is configured as an aerosol to solid surface concentrator, a mechanical means, which among others can include a simple robotic arm (not shown), delivers the concentrated sample to the cell 50. While transporting the sample, it is mixed with the EHAP and the oxygen scavenger to induce phosphorescence light associated with any biomaterial of interest, provided, of course, that the material is present in the sample.

Having delivered the sample mixed with the EHAP to the optical cell 50, the optical system, illustrated generally as 26 in FIG. 2, provides an optical analysis of the delivered sample by causing the sample to induce fluorescence and phosphorescence light signals and convert them into electrical signals. The optical system is configured to excite the sample by initially turning a light source, such as a Xenon flash lamp 52 (FIGS. 3 and 4), which generates discontinuous pulses of light incident upon the sample. As a result, if the biomaterial of interest is present, the sample emits fluorescent and possibly phosphorescent lights propagating along two optical channels, each of which includes a photo multiplier tubes (PMT) 56, 58 (FIGS. 3 and 4) amplifying signals emitted at selective frequencies.

To analyze the specimens constituting the sample, the current level applied to the lamp 52 causes the latter to emit optical energy in the ultraviolet range. To reduce the amount of dispersion, the output from lamp 52 is processed by a filter 54, so that the sample is only excited by a predetermined wavelength varying within the UV range; the filtered output is eventually focused on the cell 50 by means of an upstream lens assembly 60. To boost the signal amplitude at the integrator output, the lamp 52 preferably generates three pulses fired in rapid succession at about 25 ms intervals.

Assuming that the sample contains the bio-materials of interest capable of emitting at least fluorescent light, two optical channels of the optical system are configured to selectively pass and amplify fluorescent signals propagating at different frequencies. Based on experimentation data, the 450 nm PMT 58 optically coupled with an outlet of the first optical sub-system, which includes a filter 62 and focusing lens systems 60, generates an amplified electrical signal in response to detection fluorescence of NADH. The other optical channel includes the 360 nm PMT 56 coupled to a second optical sub-system, which is configured similarly to the first one, and used to primarily detect fluorescence. In addition, the 450 nm PMT is also capable of detecting phosphorescence of Tryptophan upon extinguishing the lamp 52 for a predetermined period of time.

It has to be noticed that all distances, including that between the optical cell 50 and the PMTs 56, 58, the optical cell and the lamp 52, have to be experimentally optimized to allow for maximum light transmission through the system. A few optional modifications of the overall optical system can include, for example, a gated PMT 59 (FIG. 3) that can be added to the 450PMT in order to control the time delay activation of the photo multiplier tube and to prevent the saturation of the phosphorescence measurement by the fluorescent signal. Another potential contribution to the saturation issue is the proper selection of the filter 62 coupled to the 450PMT; it is desirable that a filter rated at optical density (OD) 5 with about a 10 nm bandwidth be installed. The relatively high OD provides more efficient blocking of light emissions that are not within the bandwidth of interest. Note that all dimensions, ranges and numeric characteristics are subject to numerous variations, which primarily depend from the type of bio-agents to be detected.

Assuming that either two fluorescence signals have been simultaneously emitted or the fluorescence and phosphorescence light signals have been sequentially emitted, the output electrical signals of the PMTs 56, 58 are received by the electronic system 70 (FIGS. 3 and 5). The electronic system is configured to process electrical signals outputted by the PMTs 56, 58 via connectors 64 (FIG. 3) into amplifier circuits of a controller card 28 (FIG. 2) and to compare the processed signals with respective reference values. The desired sequence of actuation of pumps, valves and other components as well as automatic triggering of the more sophisticated equipment are likewise controlled by the electronic system 70.

The heart of the electronic system 70 is a processor having software executed thereon for sequentially operating the sensor 30 in a manner consistent with the inventive method 10. As is typical for the rest of the disclosed components, among a variety of suitable devices, a MC68HC11, which is an 8-bit processor chip, and three amplifier circuits control system timing and overall signal processing.

As better illustrated in FIG. 5, software executed on the processor initially actuates the mechanical system. A particular sequence of pump and valve operations depends on whether the collector 38 has an air-liquid or air-solid surface configuration. If the air-liquid surface type is incorporated in the sensor 30, initially the peristaltic pump 32 and the first pinch valve 31 are actuated in a rate- and time controlled manner to allow for the passage of liquid into the sample vessel, as indicated by a step 90. Subsequently, the vacuum pump responsible for drawing the aerosol 36 (FIG. 3) into the sample vessel is turned on to sample and collect biomaterials of interest, as indicated by a step 92. Further transportation of the concentrated sample to the optical system, is associated with the controlled actuation of the downstream pump 32 and the second valve 31 openable to provide mixing of the sample with the EHAP and the oxygen scavenger, as indicated by step 94. The latter is necessary if the sensor 30 is used to detect not only fluorescence, but phosphorescence as well.

Alternatively, if the concentrator 38 has a solid surface, the aerosol is initially forced along an impactor means at 72 to accumulate on the solid surface where the sample is mixed with the EHAP and $O_2$ scavenger injected, as shown by step 94, either directly onto the surface. Alternatively, the EHAP and $O_2$ scavenger can be added as the concentrated sample is transported, as shown by step 74, towards the photocell 50.

Upon delivery of the sample to the optical cell 50, the lamp 52 is energized in a controlled pulsed manner, as shown at 76, and if the biomaterials of interest are present in the sample, they produce a signal detected and magnified by the PMT 56. A comparator of the electronic system 70 compares the received signal with a first threshold, as shown by step 78, and if the intensity of this signal is lower than the first threshold, the mechanical system is re-activated to evacuate the sample to a sample waste reservoir 80. Note, if the sensor 30 operates only in a fluorescence vs. fluorescence mode, both PMTs 56 and 58 detect respective fluorescent signals simultaneously. Both signals propagating at different wavelength and having different intensity are compared with respective reference or threshold values. For example, the optical channel provided with the PMT 56 is operative to detect fluorescence emissions in the 360 nm-wavelength band which is associated with tryptophan and bioaerosols containing this flurophore. The other channel including the PMT 58 is operative to detect fluorescence emissions in the 450 nm-wavelength band associated with NADH and bioaerosols containing the latter.

If, however, the sensor 30 in a fluorescence vs. phosphorescence mode, the signal detected after the lamp 52 has been extinguished at 82 by the PMI 58 corresponds to a phosphorescent signal. This signal can be associated with Tryptophan phosphorescence. Similarly to the first mode of operation, in the second mode of operation, both signals—fluorescence and phosphorescence—are sequentially compared to respective thresholds. If the phosphorescence signal passes the master, as indicated by step 84, the sample is conveyed to a sample reservoir 86 where it is stored for further examination. However, even if the phosphorescence master is not passed in the second mode, the sample is still saved in the sample reservoir 86 for further detection, since it certainly contains a material, which can be of a biological origin capable of fluorescing, as determined at 78. The latter procedure is also applicable to the first mode operation, wherein as either of the two fluorescence signals at least matches a respective threshold, the sample is rerouted to the sample reservoir 86 for further detection.

Software executed on the processor, can trigger the more sophisticated detection system, as shown by step 88, which, in turn, is coupled to the sample reservoir 86 to further evaluate the stored sample. Furthermore, an audible signal generated by a piezoelectric or other type buzzer 98 and a visual signal 100 can be generated either immediately upon detecting the biomaterial of interest.

As shown in FIG. 6, it is contemplated to assemble a plurality of the sensors 30 and strategically placed them in a building or in any other "closed" space structure equipped with a central processor 102. The central processor will be able to receive a signal generated by any of the sensors 30 and identify the location of the triggered sensor. The central processor 102 can trigger the more sophisticated detection equipment 96 configured to continue the examination of the stored sample and characterized by higher sensitivity and selectivity capabilities.

Further modification of the sensor 30 may include, for example, the installation of a control panel coupled to the electronic system 70 and operative to allow the operator to manipulate variable parameters including, but not limited to the timing of the pumps for the fluidic system, the reference (alarm) threshold values, the collection time, the duration of on-state of the lamp and many others. There is an opportunity to improve the selectivity of the sensor 30 by including phosphorescence measurements or adding a particle counter. It should be understood that the inventive sensor can operate on a cyclical basis.

While the invention has been shown and described with references to certain preferred embodiments thereof, it will be understood by those skilled in the art that various changes in form and details may be made therein without departing from the spirit and scope of the invention as defined by the appended claims.

What is claimed is:

1. A sensor for detecting biomaterials of interest contained in a bioaerosol sample comprising:

a mechanical system operative to collect the bioaerosol sample;

an optical system coupled to the mechanical system and having two optical channels, the optical system including a source of light selectively energizable to excite the collected bioaerosol sample emitting at least two emission signals of different wavelengths each of which is detected by a respective one of the two optical channels;

wherein the at least two emission signals are fluorescent signals emitted simultaneously during the energization of the source of light, one of the optical channels being configured to detect a time-delayed phosphorescent emission signal generated by the bioaerosol sample upon de-energization of the source of light to allow for time resolution to be used as a discriminator between the fluorescent and phosphorescent signals, so that the sensor is provided with the improved selectivity of the detection of the biomaterials of interest; and an electronic system coupled to the mechanical and optical systems and operative to compare each of the fluorescent signals and the phosphorescent signal against a respective predetermined reference value to establish whether each of the signals is generated by the biomaterials.

2. The sensor of claim 1, wherein each of the optical channels comprises a photomultiplier tube (PMT) configured to selectively detect a respective one of the at least two emission signals and to convert the respective detected emission signal into a corresponding electrical signal.

3. The sensor of claim 2, further comprising a photocell filled with a metered amount of the bioaerosol sample and located between the source of light and the optical channels.

4. The sensor of claim 2, further comprising a filter and lens assembly located between the photocell and the source of light to allow passage of light emitted by the source of light within a UV range.

5. The sensor of claim 2, wherein the source of light is a flash lamp controllably pulsing the bioaerosol sample with light pulses, each of the optical channels further comprising a filter and a lens assembly located upstream from a respective one of the PMT and configured to allow each of the optical channels to detect a selective wavelength associated with a respective one of the at least two emission signals.

6. The sensor of claim 2, further comprising a gated PMT socket coupled to one of the PMTs and operative to control time delay activation thereof.

7. The sensor of claim 2, wherein the electronic system includes a processor and software executed on the processor for controlling timing and sequence of the mechanical and optical systems, the processor being operative to receive the electrical signals corresponding to the fluorescent signals and the phosphorescent signal and compare each to a respective threshold value, whereas if any of the compared electrical signals is at least equal to a respective threshold value, a visual and audible control signal indicating detection of the biomaterials of interest is generated.

8. The sensor of claim 7, further comprising an LCD control panel to allow modification of parameters operating the mechanical and optical systems.

9. The sensor of claim 1, wherein the mechanical system includes a sample concentrator configured to collect bioaerosol on an impaction surface, wherein the impaction surface is liquid or solid.

10. The sensor of claim 9, further comprising a plurality of reservoirs in flow communication with the concentrator and operative to store a sample fluid and chemicals adapted to mix with the collected bioaerosol sample to improve luminescent characteristics of the collected sample.

11. The sensor of claim 10, further comprising a plurality of controllably operating flow controlling components including peristaltic pumps which are located along a fluid path between the sample fluid reservoir and the concentrator and the concentrator and the chemicals reservoir and pinch valves.

12. The sensor of claim 10, wherein chemicals include an oxygen scavenger and a heavy atom perturber selected from the group consisting of potassium iodide, lead, thallium, lutetium, gallium, cesium, barium and mixtures thereof.

13. The sensor of claim 9, further comprising a vacuum pump in flow communication with the concentrator and operative to draw an aerosol into the concentrator.

* * * * *